(12) United States Patent
Blixt et al.

(10) Patent No.: US 8,342,687 B2
(45) Date of Patent: Jan. 1, 2013

(54) EYE-TRACKING USING A GPU

(75) Inventors: Peter Blixt, Hagersten (SE); Miroslav Kobetski, Danderyd (SE); Anders Hoglund, Sigtuna (SE)

(73) Assignee: Tobii Technology AB, Danderyd (SE)

( * ) Notice: Subject to any disclaimer, the term of this patent is extended or adjusted under 35 U.S.C. 154(b) by 163 days.

(21) Appl. No.: 12/893,128

(22) Filed: Sep. 29, 2010

(65) Prior Publication Data
US 2011/0085139 A1 Apr. 14, 2011

(30) Foreign Application Priority Data
Oct. 8, 2009 (EP) .................................... 09172535

(51) Int. Cl.
*A61B 3/14* (2006.01)
*A61B 3/00* (2006.01)

(52) U.S. Cl. ......................... 351/210; 351/209; 351/246

(58) Field of Classification Search ........... 351/200–246
See application file for complete search history.

(56) References Cited

U.S. PATENT DOCUMENTS

| | | | |
|---|---|---|---|
| 7,986,816 B1 * | 7/2011 | Hoanca et al. ................. | 382/115 |
| 2003/0123027 A1 | 7/2003 | Amir et al. | |
| 2004/0227699 A1 * | 11/2004 | Mitchell ......................... | 345/44 |
| 2009/0315827 A1 * | 12/2009 | Elvesjo et al. ................. | 345/157 |

OTHER PUBLICATIONS

Nico Galoppo, et al; "LU-GPU: Efficient Algorithms for Solving Dense Linear Systems on Graphics Hardware", Published in Proceeding SC '05 Proceedings of the 2005 ACM/IEEE Conference on Supercomputing, Seattle, WA, USA—Nov. 12-18, 2005, 12 pages.
Jens Kruger, et al; "Linear Algebra Operators for GPU Implementation of Numberical Algorithms", ACM Transactions on Graphics, vol. 22, No. 3, pp. 908-916, Jul. 2003.
Oscar Mateo Lozano, et al; "Simultaneous and Fast 3D Tracking of Multiple Faces in Video by GPU-Based Stream Processing", IEEE International Conference on Acoustics, Speech and Signal Processing, 2008. ICASSP 2008; Mar. 31-Apr. 4, 2008, pp. 713-716, Las Vegas, NV.
Tracy McSheery, et al.; "Enhanced Optical Tracking", SPIE, PO Box 10 Bellingham WA 98227-0010 USA, vol. 6957, 2008, pp. 69570A-1-69570A-10, XP040437215, abstract, Chapters 1., 1.2, 1.3, 2.1.

(Continued)

*Primary Examiner* — Mohammed Hasan
(74) *Attorney, Agent, or Firm* — Ladas & Parry LLP

(57) ABSTRACT

Provided is a method of determining a gaze point of an eye watching a visual display controllable by a display signal. The method comprises generating a display signal using a graphics card in order for the visual display to produce a screen pattern; receiving a signal encoding an image of the eye including a corneo-scleral reflection of the screen pattern; and determining, based on in part the geometry of said reflection, a gaze point of the eye, wherein said determining a gaze point includes utilizing the graphics card as a parallel processor.
The image of the eye may be received directly at the graphics card. The graphics card may extract image features in the eye images. Reference illuminators may be used, and the screen pattern may be interlaced with a distinctive reference pattern. Further provided are a gaze-tracking system and a personal computer system adapted to determine a gaze point of a viewer.

14 Claims, 3 Drawing Sheets

OTHER PUBLICATIONS

Yoshio Matsumoto, et al; "An algorithm for real-time stereo vision implementation of head pose and gaze direction measurement", Automatic Face and Gesture Recognition, 2000. Proceedings, Fourth IEEE International Conference on Grenoble, France Mar. 28-30, 2000, Los Alamitos, CA, USA, IEEE Comput.Soc, US, Mar. 28, 2000, pp. 499-504, XP010378305 ISBN: 978-0-7695-0580-0 abstract, Chapter 2.

Jeffrey J Kang, et al.; "Investigation of the Cross-Ratios Method for Point-of-Gaze Estimation", IEEE Transactions on Biomedical Engineering, IEEE Service Center, Piscataway, NJ, US, vol. 55, No. 9, Sep. 1, 2008, pp. 2293-2302. XP011246738, ISSN: 0018-9294, firgures 1,2; Chapter III.

European Search Report: EP 09 17 2535.

* cited by examiner

EYE-TRACKING USING A GPU

TECHNICAL FIELD

The invention disclosed herein generally relates to eye tracking (determination of gaze point or gaze angle) using a computer system. In particular, the invention provides an efficient implementation of data input, data output and data processing for determining the gaze point of an eye watching a visual display forming part of a portable or stationary personal computer system, or a communication device with imaging and computing capabilities, such as a mobile telephone.

BACKGROUND

Monitoring or tracking eye movements and detecting a person's gaze point can be used in many different contexts. Eye tracking data can be an important information source in analysing the behaviour or consciousness of the person. It can be used both for evaluating the object at which the person is looking and for evaluating the respective person. The diverse uses of gaze point detection include studies on the usability of software and different types of interfaces; evaluation of web pages, advertising and advertisements; provision of means for educating pilots in simulator environments and for training surveillance personnel in security-critical roles; and research in psychology, behavioural sciences and human perception. A field which has attracted an increasing interest in recent years is the evaluation of advertising and other marketing channels.

Eye tracking techniques can also be used for interaction: a user can control a computer by just looking at it. Eye control can be applied as sole interaction technique or combined with keyboard, mouse, physical buttons and voice. Eye control is used in communication devices for disabled persons and in various industrial and medical applications.

While eye tracking systems are utilised in a growing range of applications, they are not yet flexible enough to belong to the standard equipment of new laptops and desktops although web cameras do. Most standard-type web cameras, having a resolution of a few million pixels, would provide sufficient optical quality for eye-tracking purposes. If needed, it is easy to provide supplementary illuminators around or behind the display screen (cf. applicant's co-pending European Patent Applications EP 09 157104 and EP 09 157106, which are included herein by reference in their entirety), possibly as detachable units. However, the computational complexity of eye tracking may be enough to dissuade a computer vendor from including such capabilities, as some eye tracking implementations occupy a large part of the input/output capacity, memory resources and data processing capacity of the central processing unit (CPU) when run on a personal computer in real time. Such occupancy is detrimental to other functions of the computer; notably it may slow down execution of other processes and increase their latency. Thus, there is a need for improved computer implementations of eye tracking.

SUMMARY OF THE INVENTION

An object of the present invention is to provide an improved, more efficient computer implementation of gaze tracking of an eye watching a visual display. Another object of the present invention is to provide an implementation that, compared to available implementations, interferes less with simultaneous processes executed on the same the computer.

A further object of the invention is to provide a gaze tracking system, in which transmission, storage and processing resources are used efficiently.

Yet another object is to provide a gaze tracking system that can be integrated in a personal computer system (e.g., desktop or laptop computer, notebook, netbook, smartphone, personal digital assistant, mobile camera and other devices having a graphics card or dedicated graphical processing facility) without interfering with other tasks executed on the computer. A further object is to provide a gaze tracking system suitable for real-time operation.

At least one of these objects is achieved by a method, computer-readable medium, gaze tracking system and personal computer system, as set forth in the independent claims. The dependent claims define embodiments of the invention.

In the context of the present application, the term 'geometry' (e.g., the geometry of the corneo-scleral reflection), refers to both its size, position and shape, thus, to the totality of geometric transformations which the screen pattern undergoes at reflection. A CPU is a default data processing resource and a universal serial bus (USB) is a default interface for an imaging device. A graphics card (also known as video card, video adapter, video board, video controller, display adapter and graphics accelerator) is an integrated circuit that generates the video signal sent to a computer display. The card is usually located on the computer motherboard or is a separate circuit board, but is sometimes built into the computer display unit. It contains a digital-to-analogue module, as well as memory chips that store display data. Graphics cards are manufactured and sold under a variety of trademarks, such as FireGL™, FirePro™, Flipper™, GeForce™, Hollywood™, Mobility FireGL™, Nvidia™, Quadro™, Radeon™, Rageu™, Reality Synthesizer™, Tesla™, Xenos™ and XGPU™.

In a first aspect of the invention, there is provided a method of determining a gaze point of an eye watching a visual display, which is controllable by a display signal. The method comprises:

generating a display signal using a graphics card in order for the visual display to produce a screen pattern;

receiving a signal encoding an image of the eye including a corneo-scleral reflection of the screen pattern; and determining, based on in part the geometry of said corneo-scleral reflection of the screen pattern, a gaze point of the eye, wherein said determining a gaze point includes utilising the graphics card as a parallel processor.

The above method involves assignment of certain data processing tasks and/or certain flows of input/output data involved in eye tracking. Particularly processing tasks, to be specified in the following, are relocated from the CPU to the graphics card, or more precisely, to a graphical processing unit (GPU) within the graphics card. This offloads the CPU and liberates resources for use by other processes. Besides, if the GPU performs better than the CPU for certain processing tasks, then the relocation of such tasks is likely to improve the overall performance of the computer system. This is generally true of matrix operations, image processing, compression and decompression of images and other algorithms susceptible of being performed by parallel computing facilities. It is well-known that GPUs are generally characterised by arithmetic excellence and high memory bandwidth. More precisely, their pipeline architecture achieves high throughput at the cost of a relatively large latency; the latency time, however, is several orders of magnitude smaller than the millisecond time scale on which the human visual system operates and causes no difficulty in the eye-tracking context. From a more general point of view, there are further devices suitable for offloading the CPU, notably so-called physics modules or physics cards, whose primary use is to assist in heavy calculations involved in simulating systems according to the laws of nature. Embodiments of the present invention may thus include, after proper adaptation, a physics card in the same role as a graphics card.

Further, according to the invention, a signal encoding an image of the eye to be tracked is received at the graphics card. Because a number of preliminary processing steps can thus be performed by the graphics card, the amount of data reaching the CPU can be considerably decreased by filtering out irrelevant image segments, pre-processing the image data, extracting coordinates of image features and the like. Additionally, the fact that the image signal is received at the graphics card, where it is processed, shortens the path of the input data flow, which would otherwise be transmitted over the USB interface, the internal bus and the graphics port or over some other chain of connected motherboard devices. This efficient routing of the input data flow constitutes another advantage of the invention.

In a second aspect of the invention, there is provided a computer-program product for carrying out the above method. In a third and fourth aspect of the invention, there are provided a gaze tracking system and a personal computer system (this term is to be understood as indicated above) in which such gaze tracking system is integrated. The gaze tracking system comprises a visual display, a camera, a graphics card, and a gaze-point determining module. Here, the gaze-point determining module, which may be a software module having authority to allocate resources within the system, is operable to cause the system to function in accordance with the method set forth above. A fifth aspect of the invention relates to use of a graphics card for carrying out certain tasks in connection with gaze tracking of an eye watching a visual display.

In one embodiment of the present invention, the graphics card extracts one or more image features in the corneo-scleral reflection of the screen pattern. The graphics card then deduces the corresponding positions of the one or more image features in the screen pattern from the display signal, which is provided to the visual display by the graphics card itself. The coordinates of the image features before and after reflection in the cornea are used to determine a position of the eye. As an alternative, the display signal can be taken as starting point and regions of the screen pattern—with deformation, mirroring etc. taken into account—can be searched for in the reflection. In some embodiments, also the orientation of the eye is deduced from these coordinates.

In another embodiment, the eye is illuminated by at least one reference illuminator adapted to emit invisible light for producing a glint, a small, distinct luminous reflection on the corneo-scleral surface of the eye. The position of the glint, which is deduced from the image of the eye, is used for determining the gaze point of the eye. Wavelengths in the infrared (IR) and near-infrared (NIR) ranges are suitable for producing glints. Coaxial or non-coaxial illuminators, respectively for producing bright-pupil and dark-pupil eye images, may be applied, as considered appropriate. The reference illuminators may be integrated in the visual display or arranged thereon in a detachable fashion. Advantageously, the reference illuminators are light-emitting diodes (LEDs) provided in fittings having hooks, clips, suction cups or similar means for securing them to the visual display. As an alternative, the reference illuminators may be provided behind the display screen and aligned with suitable partial apertures provided therein, as described in EP 09 157106.

In a further embodiment, the image of the eye is received using an imaging device which is synchronised with the visual display. If the visual display responds to the display signal in real time, i.e., by plotting the image with zero or no time delay, then the display signal can be used as a trigger to the imaging device. As an alternative, a dedicated trigger signal can be provided to both devices. Synchronisation is beneficial to the image quality because aliasing-related artefacts can be avoided by sampling the display image at the same frequency as it is updated. Among such artefacts are time oscillations of the (average) image intensity and steady or moving patterns of light and dark horizontal stripes. In particular, synchronisation between the imaging device and the visual display can be used for interlacing a distinctive reference pattern with the regular screen pattern. Advantageously, the regular screen pattern to be perceived by the human viewer occupies the largest part of a cycle while the reference pattern is displayed in a short time slot, invisibly to a human eye. The reference pattern may contain image features that can be extracted easily or may be devised to facilitate measurements of the geometric deformation inflicted by the reflection. In particular, the reference pattern may include invisible light, such as NIR light, emitted by the visual display or by reference illuminators.

In an alternative embodiment, the imaging device is instead synchronised with at least one reference illuminator. Hence, as a first option, the illumination by the reference illuminator(s) can be provided in a well-defined time slot, thereby enabling energy-economical operation of the reference illuminator. As a second option, a high degree of contrast can be achieved by subtracting the respective eye images with and without illumination by the reference illuminator.

In another alternative embodiment, the imaging device, the visual display and one or more reference illuminators are all synchronised. Similarly to the interlacing of a distinct reference screen pattern, as outlined above, the visual display and the reference illuminator(s) can be operated in an alternating fashion, so as to reduce the total energy consumption and to obtain separate eye images, one with the screen reflection and one with the reference illuminator reflection.

Features from two or more of the embodiments discussed in this section can be combined without inconvenience unless they are clearly complementary. Likewise, the fact that two or more features are recited in different claims does not preclude that these can be combined to advantage.

BRIEF DESCRIPTION OF THE DRAWINGS

Embodiments of the present invention will now be described with reference to the accompanying drawings, on which.

DETAILED DESCRIPTION OF EMBODIMENTS

Figure 1:
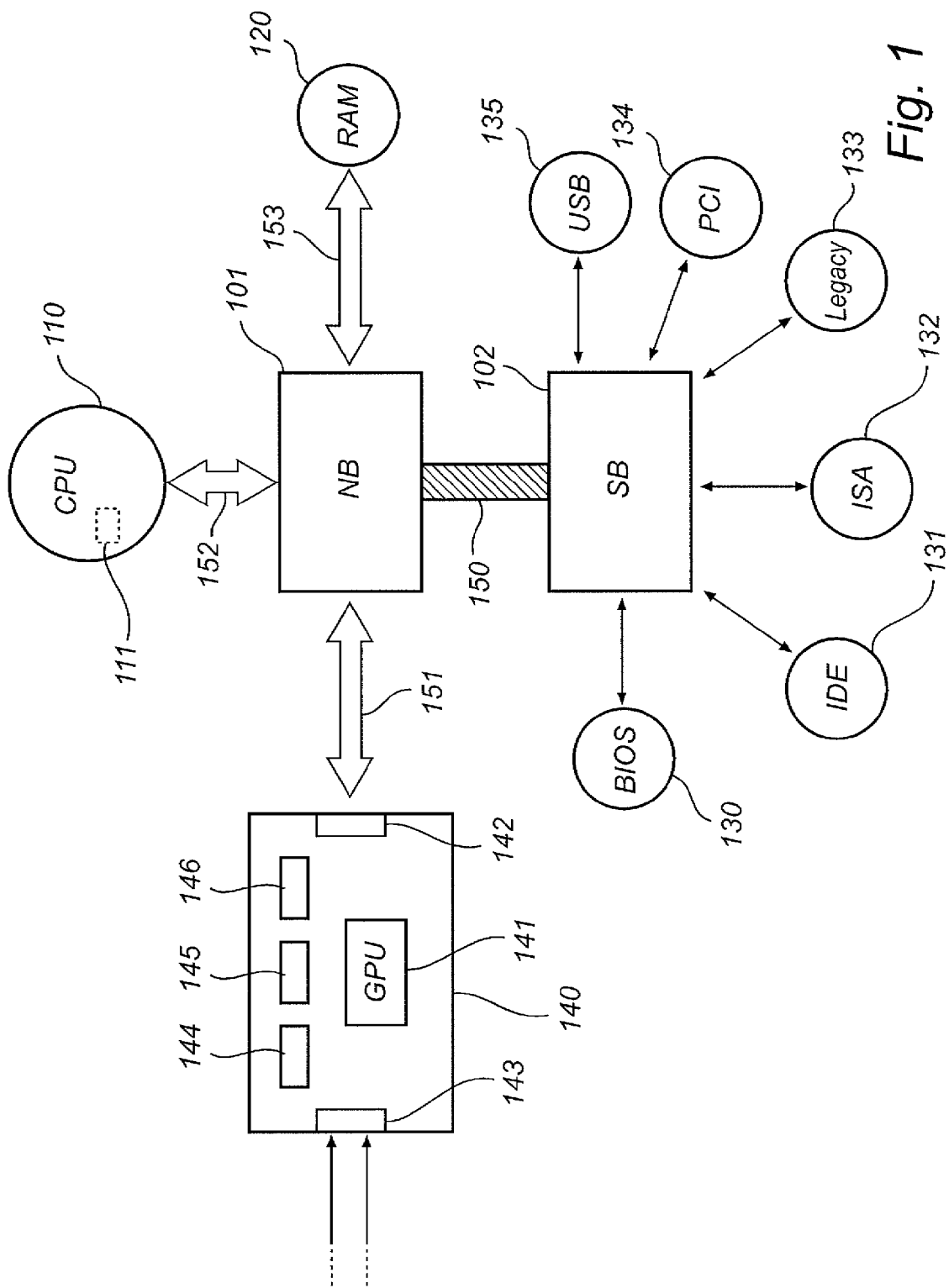
FIG. 1 is a schematic drawing of an exemplary computer motherboard and a graphics card connected thereto.

The structure of a motherboard in a typical personal computer will now be described with reference to FIG. 1. The chipset, or core logic, of the computer consists of the northbridge 101, or (integrated) memory controller, and the southbridge 102, or input/output controller hub. The northbridge 101 and southbridge 102 are communicatively connected by the internal bus 150. The southbridge 102 is generally used as an interface for devices with lower data rates than the northbridge 101. Thus, in this example, the southbridge 102 is connected to a basic input/output system (BIOS) 130, Integrated Drive Electronics (IDE) bus 131, an Industry Standard Architecture (ISA) bus 132, another legacy interface 133 to provide backward compatibility, a Peripheral Component Interconnect (PCI) bus 134 and a USB interface 135. The northbridge 101, which generally handles high-speed devices, is connected to a CPU 110 via a front-side bus 152 and to a random access memory unit 120 via a memory bus 153. Hence, for example, a data stream intended for the CPU and received at the USB interface 135 will be routed to the CPU 110 via the internal bus 150 and the front-side bus 152.

On FIG. 1, there is further indicated a graphics card 140, which is connected to the northbridge chip 101 via a graphics port 151, such as the commonly used Accelerated Graphics Port (AGP) or PCI Express (PCIe) bus. The core component of the graphics card 140 is a GPU. A motherboard interface 142 is connected to the graphics port 151. A video BIOS 144, a video memory 145 and also, if an analogue visual display is to be driven by the graphics card 140, a random access memory digital-to-analogue converter 146 form part of the graphics card 140. The graphics card 140 may comprise a media processor, such as a physics module for simulating processes according to the laws of nature. An external interface 143 allows a visual display and possibly other devices to be connected to the graphics card 140.

Figure 2:
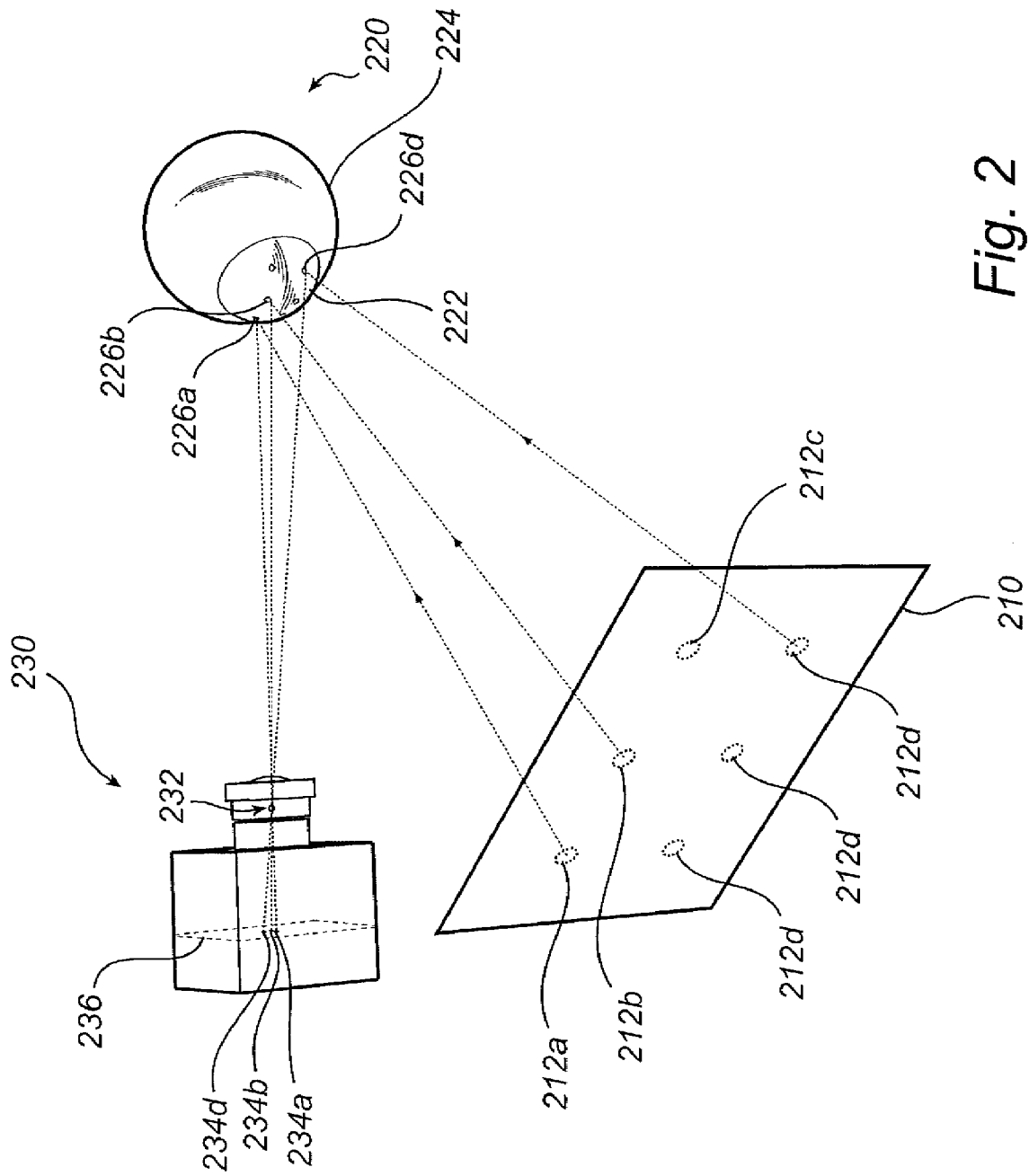
FIG. 2 is a schematic drawing of a visual display producing a screen pattern including image features which are reflected on the cornea of a viewer's eye and then recorded by an imaging device.

FIG. 2 shows the optical situation of the gaze tracking measurements. A visual display 210 produces a screen pattern including image features 212. The features 212 are imaged as corneal reflections 226 on the cornea 222 or sclera 224 of a viewer's eye 220. An imaging device 230, which is preferably a digital camera or web camera, then optically maps the corneal reflections 226 to image points 234. In a simplified model, as shown on the drawing, the imaging of the camera 230 is determined by a (rear) nodal point 232 and an image plane 236. For clearness of the drawing, only rays from image features 212a, 212b and 212d are indicated. The drawing is not to scale; in a realistic situation a 17-inch screen at 400 mm viewing distance give rise to a virtual image of the screen that is about 4 mm high.

From the positions of the image points 234, the location of the eye 220 can be computed. By finding the position of the pupil centre in the image of the eye 220, the gaze direction can be determined using the pupil-centre corneal reflection theory (see, e.g., the article by E. D. Guestrin and M. Eizenmann in *IEEE Transactions on Biomedical Engineering*, vol. 53, no. 6 (June 2006), which is included herein by reference). As an alternative, if the calculations are based on a more refined, aspherical cornea model—according to which the human cornea is not rotationally symmetric—it may be possible to find the gaze direction provided a sufficient number of pairs of image points 234 and image features 212 can be extracted (see EP 09 157106). In addition to this geometric mapping method, useful approaches for finding the gaze angle include statistical models and learning algorithms—in particular neural networks—support vector machine (SVM) methods and Viola-Jones algorithms.

Any kind of visual display 210 can be used as long as its luminosity allows the imaging device 230 to record the screen pattern reflection with sufficient image quality. As already noted, the visual display 210 may be provided with reference illuminators, possibly emitting light in an invisible wavelength range, behind or around its screen surface.

As regards the imaging device 230, both integrated and detachable devices may be used. The sensitivity wavelength range of the device is adapted according to whether the display 210 is equipped with supplementary reference illuminators. Preferably, to achieve an efficient routing of the input data flow, the imaging device 230 is connected directly to the external interface 143 of the graphics card 140, to which is connected the visual display 210 too. Alternatively, the imaging device 230 is connected by a USB (version 2.0 or 3.0) port, by an IEEE 1394 interface (FireWire) or by a CameraLink interface.

A preferred embodiment of an eye tracking system integrated in a laptop personal computer will now be described. As already noted, one can use standard visual display 210 and imaging device 230 after careful matching to the eye tracking application. In the preferred embodiment, the imaging device 230 is a camera arranged above the visual display of the computer. The sensitivity of the camera extends into the NIR range, and an NIR light source (not shown) is provided coaxially to the camera, so that a bright-pupil eye image can be provided. The camera is synchronised with the visual display and the NIR light source, such as by forwarding the clock signal (possibly amplified) of the GPU to these three devices. Whereas the visual display 210 operates at a refresh rate of 60 Hz, every $30^{th}$ cycle is used for displaying a distinctive reference pattern and for acquiring an eye image using the camera. Because the retina has a longer integration time than $\frac{1}{60}$ second, at least in normal indoors conditions of lighting, the reference pattern will not be perceived by the viewer. It is important, however, that the integration time of the camera does not exceed one cycle. This choice of parameter values apparently provides for the sampling of two eye images per seconds. The sampling rate can be increased, but possibly at the risk of a flickering screen image. Use of a faster imaging device and a display with higher refresh rate may alleviate such problems.

Figure 3:
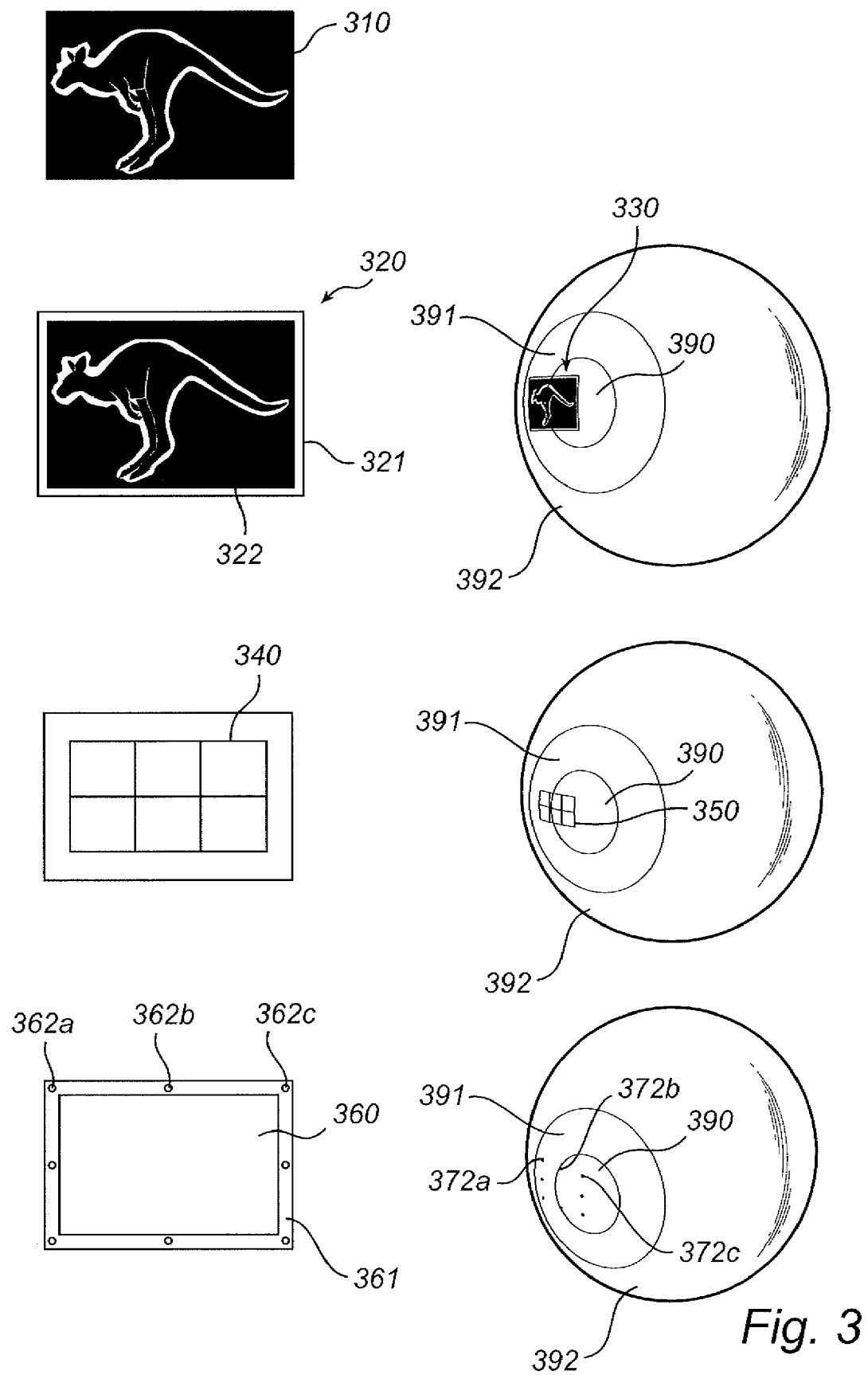
FIG. 3 shows several screen patterns and corresponding corneal reflections.

The reference pattern may be any high-contrast arrangement of easily extractable image features. For example, with reference to FIG. 3, starting from a regular screen pattern 310, a bright frame 321 (with a line width of a few millimeters) can be overlaid at the perimeter of the screen 320, leaving the inner portion 322 of the screen pattern intact. In the reflection 330 of the overlaid screen pattern, which appears on the cornea across the pupil 390 and the iris 391, the reflected bright frame 331 is easier to detect than the reflected inner portion 332 of the screen. As an alternative, a grid 340 of vertical and horizontal lines has intersections that provides distinctive control points and can be easily retrieved in the reflection 350 of the grid. The grid 340 provides additional information on the local deformation of the image, and hence of the position and orientation of the corneo-scleral surface 390, 391, 392.

As another alternative, a visual display 360, which may be a standard thin-film transistor liquid-crystal display, is surrounded by a portion 361 in which a plurality of light-emitting diodes (LEDs) 362 are arranged. Preferably, the LEDs 362 are adapted to emit NIR, and are covered by a plate that is transparent to NIR but not to light in the visible wavelength range. Thus, the LEDs 362 are hidden from a viewer of the display 360. The LEDs 362, which may be operated synchronously with the camera as outlined above, give rise to distinct reflections 372 in the corneo-scleral surface 390, 391, 392.

In the preferred embodiment, the camera is directly connected to the graphics card 140, which receives an image signal at the external interface 143. The image signal is not forwarded to the CPU directly, but is preprocessed by the GPU 141.

As a first pre-processing step, the image signal, which is provided in a compressed format to economise bandwidth in the camera-computer link, is decompressed using built-in routines of the GPU 141.

A second pre-processing step concerns subtraction and is effectuated only in bright-pupil imaging. The image used for further processing is obtained from a bright-pupil eye image acquired with the coaxial NIR light source active and a dark-pupil eye image acquired nearby in time with the light source turned off. To increase contrast, the dark-pupil image is subtracted pixel-wise from the bright-pupil image so as to bring out the NIR contribution, notably the retinal reflection through the pupil. Because the graphics card 140 contains enough memory for storing complete images, it is advantageous to perform the task of image subtraction at the graphics card 140.

In a third pre-processing step, image features in the corneo-scleral reflection are extracted and paired with corresponding coordinates in the screen pattern, in accordance with the display signal currently provided to the visual display by the graphics card 140. (Since reflection on the curved cornea surface may deform the screen pattern severely, this order of actions is preferable to extracting features from the screen pattern and retrieving these in the reflection.) The extraction of image features may use edge detection filters like Sobel filters and connected components or Canny filters or statistical methods like classification algorithms, particularly entropy-based image segmentation algorithms, which are of a parallelisable character and thus well suited for being executed by the GPU 141. Object recognition may be performed according to the teachings of chapter 7 in M. Sonka, V. Hlavac and R. Boyle, *Image processing analysis, and machine vision*, Brooks/Cole Publishing Company (1999). Moreover, the extraction may be preceded by a conditioning step of (Sobel) differentiation, some appropriate convolution or correlation operations, or histogram-based brightness correction, which are all highly parallelisable operations. In bright-pupil images, the pupil-centre coordinates are retrieved similarly. It is noted that reference illuminators, if such are provided, and their corneo-scleral glints can be included in the data processing in an analogous manner as image features, in this step as well as in the subsequent ones.

The pairs of coordinates of image features and their reflections are used for computing the gaze direction, that is, the actual position of the visual axis of the eye. The computations may further take the pupil-centre coordinates into account. The computational tasks associated with geometric mapping methods are outlined in section II of the work by Guestrin and Eizenman, and include operations on both scalars and matrices. The estimation of cornea position and cornea orientation involves solving systems of linear equations, in particular over-determined systems.

A gaze-point determining module 111, which may be a hardware module but is preferably a software program executed by the CPU 110, is authorised by the operating system of the computer to allocate the data processing and storage tasks in the eye tracking and to route the input/output data flows. As a general rule—which should be adapted to the actual GPU used—occasional scalar operations are handled more efficiently by the CPU 110, while matrix computations and other numerical linear algebra operations are best performed by the GPU 141, which is often capable of avoiding iterative processing. It is noted that some available GPUs perform optimally for matrices that are square or have certain dimension; the matrices can then be given the desired form by padding the data entries with zeros. Regarding possible implementations of linear algebra routines in a GPU, reference is made to J. Krüger and R. Westermann, "Linear algebra operators for GPU implementation of numerical algorithms", *ACM Trans. Graph.*, vol. 22, no. 3 (July 2003) and N. Galoppo et al., "LU-GPU: Efficient algorithms for solving dense linear systems on graphics hardware", *Proc. ACM/IEEE Conf. Supercomput.*, November 2005, both of which are included herein by reference in their entirety.

As an alternative, the location and orientation of the cornea are found using built-in ray-tracing routines in the GPU 141. Indeed, by requiring light rays connecting the image features 212 and corresponding points in the image plane 236 of the imaging device 230 to pass via reflection on the cornea 222, the location and orientation of the latter is well defined once a sufficient number of image features 212 are known. Finding the cornea can take place as an iterative process, in which location and orientation parameters are successively refined until the image features and reflections match each other within a desired tolerance. Many available GPUs offer very fast hard-wired or soft-wired ray-tracing routines, which implies that high accuracy can be achieved in limited time.

As regards other approaches to calculating the gaze angle, it is preferable to express the computations in a form suitable for parallel computing, such as stream programming. As an example, the parallelisation of a Viola-Jones algorithm is discussed in O. Mateo Lozano and K. Otsuka, *Simultaneous and fast 3D tracking of multiple faces in video by GPU-based stream processing*, International Conference on Acoustics, Speech, and Signal Processing 2008.

The visual axis of the eye is deduced from the location and orientation of the cornea, possibly supplemented by the pupil-centre location, and the gaze point is the intersection of the visual axis and the display screen surface.

In steady-state operation of the eye-tracking system according to the preferred embodiment, the procedure outlined in the last few paragraphs is repeated for each eye image or even performed in a streaming fashion. Characteristic of the eye tracking system is that the CPU 110 executes a comparatively small part of the computations and, further, that the eye tracking processes only makes a limited contribution to the data flow between the graphics card 140 and the CPU 110 via the northbridge 101.

While the invention has been illustrated and described in detail in the drawings and foregoing description, such illustration and description are to be considered illustrative or exemplary and not restrictive; the invention is not limited to the disclosed embodiments. For example, embodiments of the present invention can also include dual imaging devices in order to increase image contrast or to enable simultaneous imaging coaxially and non-coaxially with the light source. By providing wavelength filters at the imaging devices, corneo-scleral reflections in different wavelength ranges can be efficiently separated. Likewise, the processing tasks of the gaze tracking computations can be apportioned between the CPU and the graphics card in a different manner than disclosed herein depending on the characteristics of these devices in a particular application.

Other variations to the disclosed embodiments can be understood and effectuated by those skilled in the art in practicing the claimed invention, from a study of the drawings, the disclosure, and the appended claims. In the claims, the word 'comprising' does not exclude other elements or steps, and the indefinite article 'a' or 'an' does not exclude a plurality. A single processor or other unit may fulfil the functions of several items received in the claims. The mere fact that certain measures are recited in mutually different dependent claims does not indicate that a combination of these measured cannot be used to advantage. A computer program may be stored or distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A method of determining a gaze point of an eye watching a visual display controllable by a display signal, the method comprising:
   generating a display signal using a graphics card in order for the visual display to produce a screen pattern;
   receiving a signal encoding an image of the eye including a corneo-scleral reflection of the screen pattern; and
   determining, based on in part the geometry of said corneo-scleral reflection of the screen pattern, a gaze point of the eye,
   wherein said determining a gaze point includes utilizing the graphics card as a parallel processor,
   wherein the graphics card receives, directly from the imaging device, the signal encoding an image of the eye including a corneo-scleral reflection of the screen pattern, and
   wherein said determining a gaze point comprises:
      extracting, using the graphics card, one or more image features in said corneo-scleral reflection of the screen pattern; and
      comparing, using the graphics card, said one or more image features with the display signal in order to retrieve these in the screen pattern.

2. A method according to claim 1, further comprising:
   illuminating the eye by invisible light from at least one reference illuminator,
   wherein:
   the image of the eye further includes a glint produced by said at least one reference illuminator; and
   said determining a gaze point is further based on the position of the glint.

3. A method according to claim 1, wherein the image of the eye is received from an imaging device which is synchronized with the visual display and/or a reference illuminator.

4. A method according to claim 2, wherein the image of the eye is received from an imaging device which is synchronized with the visual display and/or a reference illuminator.

5. A method according to claim 3 or 4, further comprising:
   repeatedly interlacing the screen pattern with a distinctive reference pattern.

6. A method according to claim 1, wherein said receiving an image comprises decompressing a compressed image format.

7. A computer-readable medium containing instructions which when executed on a general-purpose computer perform the method of claim 1.

8. A gaze tracking system, comprising:
   a visual display controllable by a display signal;
   an imaging device adapted to image the face of a viewer of the visual display; and
   a graphics card adapted to generate a display signal for causing said visual display to produce a screen pattern,
   said system characterized in a gaze-point determining module adapted to use the graphics card as a parallel processor to determine a gaze point of the viewer's eye based on in part the geometry of a corneo-scleral reflection of the screen pattern using an image of the viewer's eye containing said corneo-scleral reflection of the screen pattern, said image being received from the imaging device,
   wherein the gaze-point determining module is operable to cause the graphics card to receive, directly from the imaging device, an image of the viewer's eye containing a cornea-scleral reflection of the screen pattern, and
   wherein the graphics card is further adapted to:
   extract image features in said corneo-scleral reflection of the screen pattern; and
   compare said image features with the display signal in order to retrieve these in the screen pattern.

9. A gaze tracking system according to claim 8, further comprising one or more reference illuminators, each being adapted to emit invisible light in order to produce a glint on a viewer's eye,
   wherein the gaze tracking system is adapted to determine a gaze point of the viewer's eye further based on the position of the glint.

10. A gaze tracking system according to claim 9, wherein said one or more reference illuminators are detachable.

11. A gaze tracking system according to claim 9, wherein the imaging device is synchronized with the visual display and/or a reference illuminator.

12. A gaze tracking system according to claim 8, wherein the imaging device is synchronized with the visual display and/or a reference illuminator.

13. A gaze tracking system according to claim 12 or 11, wherein the graphics card is adapted to repeatedly interlace the screen pattern of the visual display with a distinctive reference pattern.

14. A personal computer system comprising a gaze tracking system according to claim 8.

* * * * *